US012194029B1

(12) United States Patent
Venugopala et al.

(10) Patent No.: US 12,194,029 B1
(45) Date of Patent: Jan. 14, 2025

(54) ETHYL-1-(SUBSTITUTEDBENZOYL)-5-METHYLPYRROLO[1,2-A]QUINOLINE-3-CARBOXYLATES AS ANTICANCER AGENTS

(71) Applicant: KING FAISAL UNIVERSITY, Al-Ahsa (SA)

(72) Inventors: Katharigatta N. Venugopala, Al-Ahsa (SA); Vijaykumar Uppar, Godihal (IN); Rashmi Venugopala, Durban (ZA); Sandeep Chandrashekharappa, Lucknow (IN); Basavraj Padmashali, Godihal (IN); Viresh Mohanlall, Durban (ZA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 26 days.

(21) Appl. No.: 18/383,407

(22) Filed: Oct. 24, 2023

(51) Int. Cl.
*A61K 31/437* (2006.01)
*A61P 35/00* (2006.01)

(52) U.S. Cl.
CPC ............ *A61K 31/437* (2013.01); *A61P 35/00* (2018.01)

(58) Field of Classification Search
CPC .............................. A61K 31/437; A61P 35/00
See application file for complete search history.

(56) References Cited

U.S. PATENT DOCUMENTS

2005/0014759 A1* 1/2005 Cai .................... A61K 31/4985
514/250

OTHER PUBLICATIONS

Zhong, L. et al. "Small molecules in targeted cancer therapy: advances, challenges, and future perspectives." Signal transduction and targeted therapy, 2021. vol. 6(1), 201: 1-48. (Year: 2021).*
Coussens, N. P. et al. "Small-Molecule Screens: A Gateway to Cancer Therapeutic Agents with Case Studies of Food and Drug Administration—Approved Drugs." Pharmacological reviews, 2017. vol. 69(4): 479-496. (Year: 2017).*
Patani, G. A. et al. "Bioisosterism: A Rational Approach in Drug Design." Chemical reviews 1996, vol. 96, 8: 3147-3176. (Year: 1996 ).*
Uppar, V. et al. Synthesis and characterization of pyrrolo[1,2-a]quinoline derivatives for their larvicidal activity against Anopheles arabiensis. Struct Chem, 2021. vol. 31: 1533-1543. (Year: 2021).*
Li, Y. et al. 3,3-Dimethyl-1H-pyrrolo[3,2-g]quinolin-2(3H)-one derivatives as novel Raf kinase inhibitors. Med. Chem. Commun., 2013. vol. 4, 2: 367-370. (Year: 2013).*
El-Fadl, H. M.A. et al. Effective Targeting of Raf-1 and Its Associated Autophagy by Novel Extracted Peptide for Treating Breast Cancer Cells. Front Oncol., 2021. vol. 11:682596. (Year: 2021).*
Kemnitzer, W. et al. Discovery of 1-benzoyl-3-cyanopyrrolo[1,2-a]quinolines as a new series of apoptosis inducers using a cell- and caspase-based high-throughput screening assay. 2: Structure-activity relationships of the 4-, 5-, 6-, 7- and 8-positions. Bioorg Med Chem Lett. vol. 19(13): 3481-4. (Year: 2009).*
Lucescu, L. et al. Synthesis and Biological Evaluation of Some New Indolizine Derivatives as Antitumoral Agents. Letters in drug design & discovery, 2016. vol. 13, No. 6: 479-488. (Year: 2016).*
Amarandi, R. et al. Exploring Pyrrolo-Fused Heterocycles as Promising Anticancer Agents: An Integrated Synthetic, Biological, and Computational Approach. Pharmaceuticals (Basel, Switzerland). vol. 16, 6: 865: 1-30. Published on Jun. 11, 2023. (Year: 2023).*
Venugopala, Katharigatta N., et al. "Cytotoxicity and antimycobacterial properties of pyrrolo [1, 2-a] quinoline derivatives: Molecular target identification and molecular docking studies." Antibiotics 9.5 (2020): 233.
Uppar, Vijayakumar, et al. "Investigation of antifungal properties of synthetic dimethyl-4-bromo-1-(substituted benzoyl) pyrrolo [1, 2-a] quinoline-2, 3-dicarboxylates analogues: Molecular docking studies and conceptual DFT-based chemical reactivity descriptors and pharmacokinetics evaluation." Molecules 26.9 (2021): 2722.
Sechi, Mario, et al. "Design and synthesis of novel dihydroquinoline-3-carboxylic acids as HIV-1 integrase inhibitors." Bioorganic & medicinal chemistry 17.7 (2009): 2925-2935.
Gomha, Sobhi M., and Kamal M. Dawood. "Synthesis of novel indolizine, pyrrolo [1, 2-a] quinoline, and 4, 5-dihydrothiophene derivatives via nitrogen ylides and their antimicrobial evaluation." Journal of Chemical Research 38.9 (2014): 515-519.
Dawood, Kamal M., Eman A. Ragab, and Nabila A. Khedr. "Facile Access to Benzothiazole-Containing Pyrrolo [1, 2-a] quinolines and Pyrrolo [2, 1-a] isoquinolines via Nitrogen Ylides." Journal of the Chinese Chemical Society 56.6 (2009): 1180-1185.
Dawood, Kamal M., Eman A. Ragab, and Sanaa N. Mohamed. "Synthesis of Some New Indolizine and Pyrrolo [1, 2-a] quinoline Derivatives via Nitrogen Ylides." Zeitschrift für Naturforschung B 64.4 (2009): 434-438.
Pramod N Patil; Anti-Alzheimer's and Anti-Fungal Activities of Pyrrolo[1,2-a] Quinoline Derivatives; 10.22376/ijlpr.ijipr 2023; doi 2023.13.6.P1-P11.

* cited by examiner

*Primary Examiner* — Amy L Clark
*Assistant Examiner* — Chihyi Lee
(74) *Attorney, Agent, or Firm* — Nath, Goldberg & Meyer; Joshua B. Goldberg

(57) ABSTRACT

Methods of treating cancer in a patient by administering ethyl-1-(substituted benzoyl)-5-methylpyrrolo[1,2-a]quinoline-3-carboxylates to a patient in need thereof.

11 Claims, No Drawings

ETHYL-1-(SUBSTITUTEDBENZOYL)-5-METHYLPYRROLO[1,2-A]QUINOLINE-3-CARBOXYLATES AS ANTICANCER AGENTS

BACKGROUND

1. Field

The present disclosure provides ethyl-1-(substituted benzoyl)-5-methylpyrrolo[1,2-a]quinoline-3-carboxylates derivatives that are active as anticancer agents.

2. Description of the Related Art

Non-steroidal anti-inflammatory drugs (NSAIDs) have been therapeutically used in the medication of rheumatic arthritis and also in the treatment of various inflammatory disorders. Due to their gastrointestinal side effects, they are often used in limited numbers. In addition, effective anti-cancer medicines are still needed, as cancer remains a prevalent and hard to treat disease throughout the world.

Thus, there exists a need to develop anti-inflammatory and anticancer agents solving the above-mentioned problems.

SUMMARY

This compounds described herein pertain to the field of pharmaceuticals, particularly to ethyl-1-(substituted benzoyl)-5-methylpyrrolo[1,2-a]quinoline-3-carboxylates, the process of synthesis thereof, compositions including these compounds, and the use of the compounds as anticancer agents.

In an effort to develop novel anticancer agents, a series of ethyl-1-(substituted benzoyl)-5-methylpyrrolo[1,2-a]quinoline-3-carboxylates has been achieved by a synthetic chemical method and purified by the column chromatographic method. The compounds are obtained in good yields, and the synthetic method used was advantageous. Structural elucidation of the compounds is completed by spectral techniques, and the compounds are evaluated with, for example, human breast cancer and lung cancer cell lines and are found to have potential anticancer activity. Some compounds show promising anticancer activity between millimolar to micromolar concentrations compared to standard anticancer drugs.

In an embodiment, the present subject matter relates to a method of treating cancer in a patient, the method comprising administering a therapeutically effective of a compound to a patient in need thereof, the compound having the formula I:

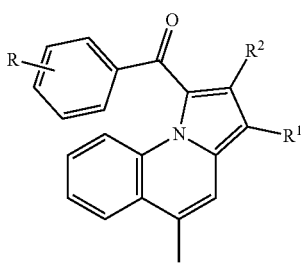

or a pharmaceutically acceptable salt, ester, stereoisomer, or solvate thereof, wherein:
one or more R groups can be attached to the phenyl ring, wherein each R is independently selected from the group consisting of hydrogen, one or more halogens, cyano, nitro, and trihalomethyl;
$R_1$ is —COOCH$_3$ or —COOCH$_2$CH$_3$; and
$R_2$ is hydrogen or —COOCH$_3$.

In another embodiment, the present subject matter relates to a method of treating cancer in a patient, the method comprising administering a therapeutically effective of a compound to a patient in need thereof, the compound having the formula I:

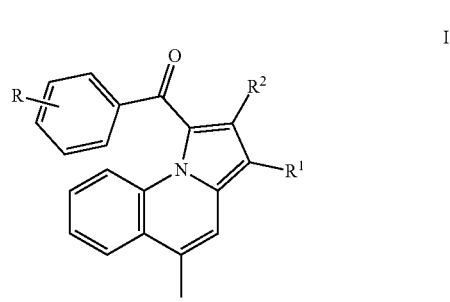

or a pharmaceutically acceptable salt, ester, stereoisomer, or solvate thereof, wherein:
one or more R groups can be attached to the phenyl ring, wherein each R is independently selected from the group consisting of hydrogen, fluorine, bromine, cyano, nitro, and trifluoromethyl;
$R_1$ is —COOCH$_3$ or —COOCH$_2$CH$_3$; and
$R_2$ is hydrogen or —COOCH$_3$.

In an embodiment, the present subject matter relates to a method of treating cancer in a patient, the method comprising administering a therapeutically effective of a compound to a patient in need thereof, the compound being selected from the group consisting of: Dimethyl-1-(3,5-bis(trifluoromethyl)benzoyl)-5-methylpyrrolo[1,2-a]quinoline-2,3-dicarboxylate (3a), Ethyl-1-(3,5-bis(trifluoromethyl)benzoyl)-5-methylpyrrolo[1,2-a]quinoline-3-carboxylate (3b), Dimethyl-5-methyl-1-(2-nitrobenzoyl)pyrrolo[1,2-a]quinoline-2,3-dicarboxylate (3c), Ethyl-5-methyl-1-(2-nitrobenzoyl)pyrrolo[1,2-a]quinoline-3-carboxylate (3d), Ethyl 1-(4-bromobenzoyl)-5-methylpyrrolo[1,2-a]quinoline-3-carboxylate (3e), Dimethyl-1-(4-cyanobenzoyl)-5-methylpyrrolo[1,2-a]quinoline-2,3-dicarboxylate (3f), Dimethyl-1-benzoyl-5-methylpyrrolo[1,2-a]quinoline-2,3-dicarboxylate (3g), Ethyl-1-benzoyl-5-methylpyrrolo[1,2-a]quinoline-3-carboxylate (3h), Dimethyl-1-(4-fluorobenzoyl)-5-methylpyrrolo[1,2-a]quinoline-2,3-dicarboxylate (3i), and a pharmaceutically acceptable salt, ester, stereoisomer, or solvate thereof.

In an embodiment, the present subject matter relates to a process for the synthesis of the compounds of formula I, including a number of species or specific structures falling under structural formula I. Further contemplated herein are pharmaceutical compositions containing these compounds, as well as methods of treating cancer by administering the present compositions to a patient in need thereof, including but not limited to breast cancer and lung cancer, by administering the present compounds to a patient in need thereof.

These and other features of the present subject matter will become readily apparent upon further review of the following specifications.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, iodo, and bromo.

As used herein, "heteroatom" refers to an atom of any element other than carbon or hydrogen and includes, for example, nitrogen, oxygen, silicon, sulfur, phosphorus, and selenium.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as cancer.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a method of treating cancer in a patient, the method comprising administering a therapeutically effective of a compound to a patient in need thereof, the compound having the formula I:

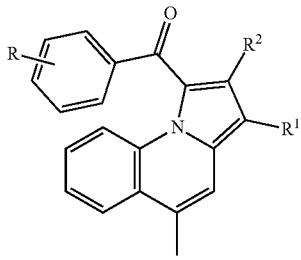

or a pharmaceutically acceptable salt, ester, stereoisomer, or solvate thereof, wherein:
one or more R groups can be attached to the phenyl ring, wherein each R is independently selected from the group consisting of hydrogen, one or more halogens, cyano, nitro, and trihalomethyl;
$R_1$ is —COOCH$_3$ or —COOCH$_2$CH$_3$; and
$R_2$ is hydrogen or —COOCH$_3$.

In one embodiment, R can be selected from the group consisting of hydrogen, trifluoromethyl, NO$_2$, CN, bromine, and fluorine. In certain embodiments, one or two R groups can be attached to the phenyl ring. In this regard, in an embodiment, when two R groups are attached to the phenyl ring, they can both be trifluoromethyl. In an additional embodiment, when one R group is attached to the phenyl ring, it can be hydrogen, NO$_2$, CN, bromine, or fluorine.

In another embodiment, R can be selected from the group consisting of hydrogen, 3,5-bis(trifluoromethyl), 4-CN, 4-Br, 2-NO$_2$, and 4-F.

In an additional embodiment, $R_1$ and $R_2$ can both be —COOCH$_3$.

In a further embodiment, when $R_1$ and $R_2$ are both —COOCH$_3$, R can be 3,5-bis(trifluoromethyl), 2-NO$_2$, 4-CN, hydrogen, and 4-F.

In another embodiment, when $R_1$ is —COOCH$_2$CH$_3$ and $R_2$ is hydrogen, R can be selected from the group consisting of 3,5-bis(trifluoromethyl), 2-NO$_2$, 4-Br, and hydrogen.

In another embodiment, the present subject matter relates to a method of treating cancer in a patient, the method comprising administering a therapeutically effective of a compound to a patient in need thereof, the compound having the formula I:

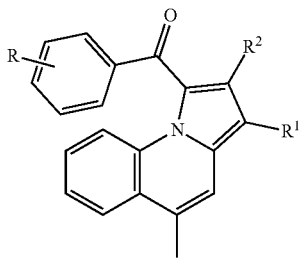

or a pharmaceutically acceptable salt, ester, stereoisomer, or solvate thereof, wherein:
one or more R groups can be attached to the phenyl ring, wherein each R is independently selected from the group consisting of hydrogen, fluorine, bromine, cyano, nitro, and trihalomethyl;
$R_1$ is —COOCH$_3$ or —COOCH$_2$CH$_3$; and
$R_2$ is hydrogen or —COOCH$_3$.

In an embodiment, the present subject matter relates to a method of treating cancer in a patient, the method comprising administering a therapeutically effective of a compound to a patient in need thereof, the compound being selected from the group consisting of: Dimethyl-1-(3,5-bis(trifluoromethyl)benzoyl)-5-methylpyrrolo[1,2-a]quinoline-2,3-dicarboxylate (3a), Ethyl-1-(3,5-bis(trifluoromethyl)benzoyl)-5-methylpyrrolo[1,2-a]quinoline-3-carboxylate (3b), Dimethyl-5-methyl-1-(2-nitrobenzoyl)pyrrolo[1,2-a]quinoline-2,3-dicarboxylate (3c), Ethyl-5-methyl-1-(2-nitrobenzoyl)pyrrolo[1,2-a]quinoline-3-carboxylate (3d), Ethyl 1-(4-bromobenzoyl)-5-methylpyrrolo[1,2-a]quinoline-3-carboxylate (3e), Dimethyl-1-(4-cyanobenzoyl)-5-methylpyrrolo[1,2-a]quinoline-2,3-dicarboxylate (3f), Dimethyl-1-benzoyl-5-methylpyrrolo[1,2-a]quinoline-2,3-dicarboxylate (3g), Ethyl-1-benzoyl-5-methylpyrrolo[1,2-a]quinoline-3-carboxylate (3h), Dimethyl-1-(4-fluorobenzoyl)-5-methylpyrrolo[1,2-a]quinoline-2,3-dicarboxylate (3i), and a pharmaceutically acceptable salt, ester, stereoisomer, or solvate thereof.

Said differently, the present subject matter can relate to methods of treating cancer in a patient by administering compounds of formula I selected from the group consisting of:

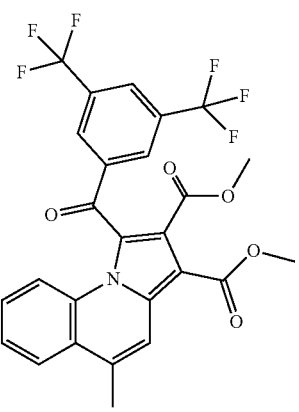

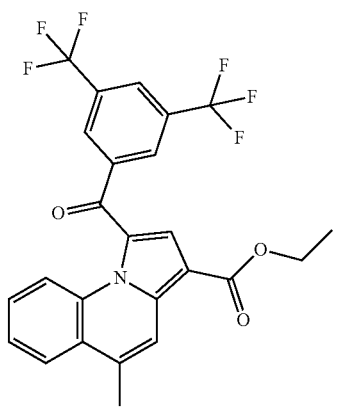

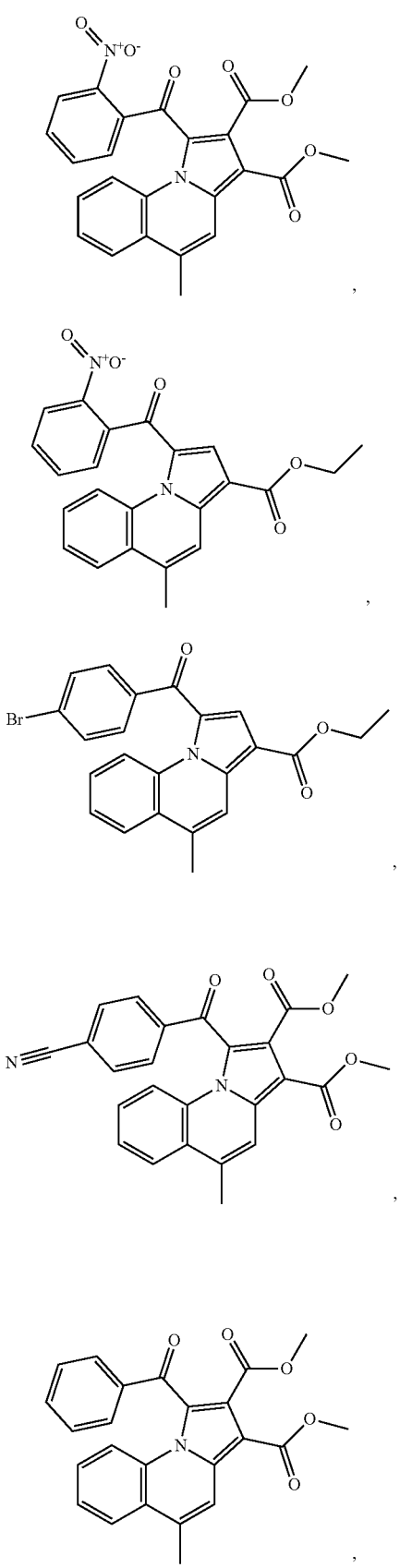

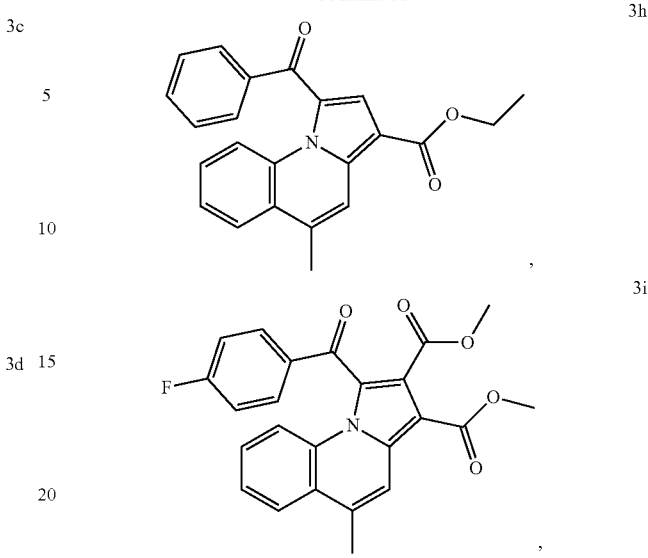

and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following general synthetic pathway. Specifically, dry DMF is added to a stirred solution of 1-[2-(4-bromophenyl)-2-oxoethyl]-4-methylquinolin-1-ium bromide (Ia), ethyl propionate (2), and $K_2CO_3$ and stirred at room temperature for about 30 minutes. Reaction completion is monitored, for example, by TLC. After completion, the reaction mixture is evaporated under reduced pressure and diluted with ethyl acetate. The ethyl acetate layer is washed with brine, water, and dried with anhydrous sodium sulfate. The ethyl acetate is removed under reduced pressure, and the crude compound is purified to obtain, e.g., ethyl-1-(4-bromobenzoyl)-5-methylpyrrolo[1,2-a]quinoline-3-carboxylate.

The synthetic strategy adopted is illustrated in Scheme 1.

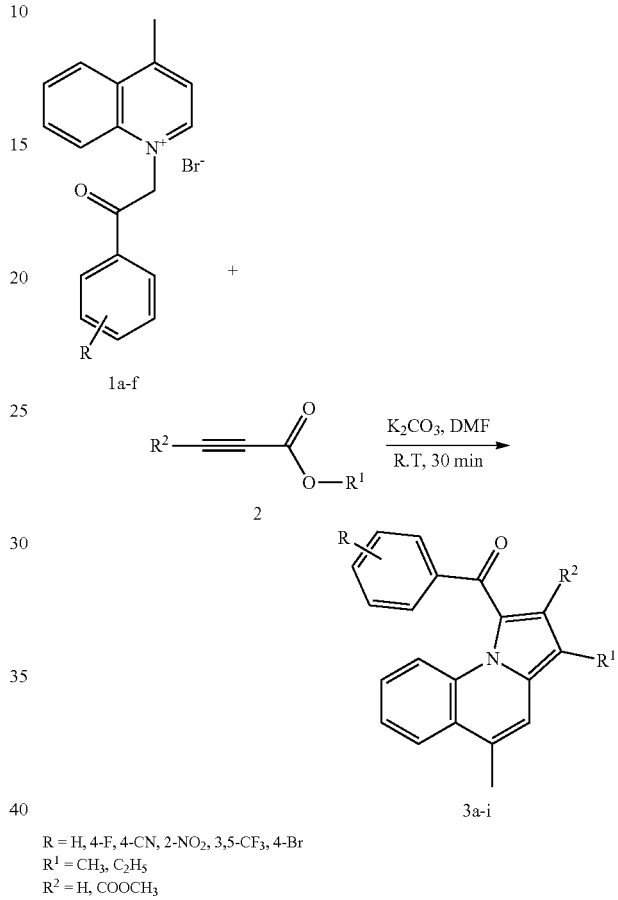

R = H, 4-F, 4-CN, 2-NO$_2$, 3,5-CF$_3$, 4-Br
R$^1$ = CH$_3$, C$_2$H$_5$
R$^2$ = H, COOCH$_3$

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one, two, or more of the present compounds, or one of the present compounds.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for cancer. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of cancer, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained-release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained-release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid, or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol, or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds for the treatment of cancer. Specifically, the present compounds can be used to inhibit cell growth of cancer cells in a patient.

Accordingly, in an embodiment of the present subject matter, the present compounds, as described herein, are engaged for in vitro study against breast cancer (as tested in the MCF-7 cell line) and lung cancer, or adeno carcinomic human alveolar basal epithelial cancer, (as tested in the A-549 cell line). Accordingly, the present compounds can be used to treat breast cancer and/or lung cancer.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one, two, or more of the present compounds are used, or one of the present compounds is used. Similarly, one or more of the present compounds can be used in combination therapy with one or more additional active agents.

The following examples relate to various methods of manufacturing certain specific compounds as described herein. All compound numbers expressed herein are with reference to the synthetic pathway figures shown above.

EXAMPLES

Example 1

Preparation of ethyl 1-(4-bromobenzoyl)-5-methylpyrrolo[1,2-a]quinoline-3-carboxylate (3e To a stirred solution of 1-[2-(4-bromophenyl)-2-oxoethyl]-4-methylquinolin-1-ium bromide (1a) (1 g, 0.00237 mol), ethyl propiolate (2) (0.232 g, 0.00237 mol), and $K_2CO_3$ (0.819 g, 0.00593 mol) was added dry DMF, and stirred at room temperature for 30 min. Reaction completion was monitored by TLC. After completion, the reaction mixture was evaporated under reduced pressure and diluted with ethyl acetate. The ethyl acetate layer was washed with brine, water, and dried with anhydrous sodium sulfate. The ethyl acetate was removed under reduced pressure, and the crude compound was purified with a column chromatography using 60-120 mesh silica gel with ethyl acetate and hexane (7:3) as eluent to afford 0.30 g (53% yield) of ethyl-1-(4-bromobenzoyl)-5-methylpyrrolo[1,2-a]quinoline-3-carboxylate. The remaining compounds (3a-d and 3f-i) were prepared following a similar protocol and the characterization details are reported below.

Example 2

Dimethyl-1-(3,5-bis(trifluoromethyl)benzoyl)-5-methylpyrrolo[1,2-a]quinoline-2,3-dicarboxylate (3a

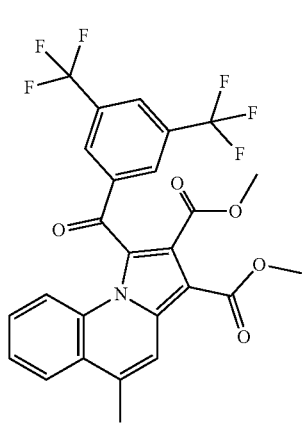

3a

Appearance; yellow color; FT-1R (neat cm$^{-1}$); 1785, 1780, 1743, 1706, 1650, 1620; $^1$H-NMR (800 MHz, CDCl$_3$); δ=8.55 (2H, s, Ar—H, Ar—H), 8.21 (1H, s, Ar—H), 8.19 (1H, s, H), 8.02-8.01 (1H, m, H), 7.67-7.66 (1H, m, H). 7.58-7.54 (2H, m, H), 3.92 (3H, s, OCH$_3$), 3.45 (3H, s, OCH$_3$), 2.75 (3H, s, CH$_3$); $^{13}$C-NMR (200 MHz, CDCl$_3$); 183.2, 165.3, 163.3, 139.6, 138.8, 137.4, 132.3, 132.2, 132.1, 132.0, 131.4, 129.8, 129.0, 126.4, 126.0, 125.8, 125.8, 123.9, 123.4, 122.1, 119.7, 117.0, 105.0, 52.4, 51.8, 19.6; LC-MS (ESI, positive): m/z=538.2 (M+H)$^+$; Anal. calcd for $C_{26}H_{17}F_6NO_5$; C, 58.11, H, 3.19, N, 2.61; found C, 58.06, F, 3.21, N, 2.58.

Example 3

Ethyl-1-(3,5-bis(trifluoromethyl)benzoyl)-5-methylpyrrolo[1,2-a]quinoline-3-carboxylate (3b

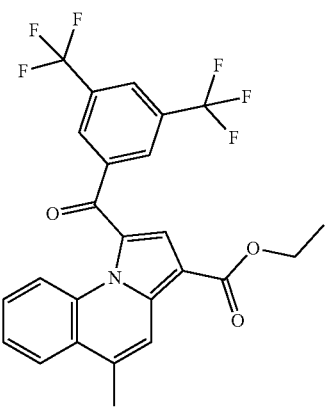

3b

Appearance; yellow color; FT-IR (neat cm$^{-1}$); 1785, 1780, 1709, 1639; $^1$H-NMR (800 MHz, CDCl$_3$); δ=8.55 (2H, s, Ar—H), 8.03 (1H, s, H), 8.02-8.01 (1H, m, H), 7.66 (1H, m, H), 7.66 (1H, s, Ar—H), 7.65 (1H, s, H), 7.63-7.58 (2H, m, H), 4.42-4.38 (2H, q, J=7.2 Hz, CH$_2$), 2.76 (3H, s, CH$_3$), 1.42-1.40 (3H, t, J=7.2 Hz, CH$_3$); $^{13}$C-NMR (200 MHz, CDCl$_3$); 180.7, 163.7, 141.5, 140.8, 137.9, 132.8, 132.4, 132.2, 132.04, 131.8, 130.9, 130.0, 129.8, 128.7, 126.5, 120.8, 125.5, 125.4, 123.8, 122.0, 120.4, 117.2, 107.6, 60.3, 19.6, 14.4; LC-MS (ESI, positive): m/z=494.2 (M+H)+; Anal. calcd for C$_{25}$H$_{17}$F$_6$NO$_3$; C, 60.86, H, 3.47, N, 2.84; found C, 60.88, H, 3.43, N, 2.81.

Example 4

Dimethyl-5-methyl-1-(2-nitrobenzoyl)pyrrolo[1,2-a]quinoline-2,3-dicarboxylate (3c

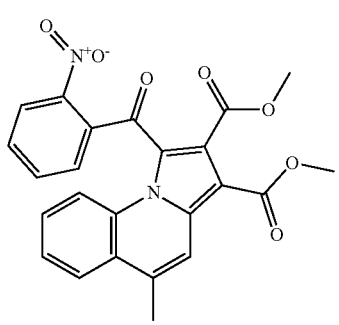

3c

Appearance; yellow color; FT-IR (neat cm$^{-1}$); 2951, 1726, 1702, 1633, 1605, 1556; $^1$H-NMR (800 MHz, CDCl$_3$); δ=8.15 (1H, m, H), 8.01-7.95 (2H, m, Ar—H), 7.63-7.62 (1H, m, H), 7.51-7.50 (1H, s, H), 7.49 (1H, m, H), 7.48-7.37 (3H, m, Ar—H), 3.92 (3H, s, COOCH$_3$), 3.45 (3H, s, COOCH$_3$), 2.70 (3H, s, CH$_3$); $^{13}$C-NMR (200 MHz, CDCl$_3$); 187.4, 165.3, 163.8, 137.7, 137.4, 135.5, 133.7, 132.3, 129.8, 128.7, 128.6, 128.5, 126.0, 125.6, 125.5, 119.5, 117.3, 104.4, 52.2, 51.6, 19.5; LC-MS (ESI, positive): m/z=447.2 (M+H)$^+$; Anal. calcd for C$_{24}$H$_{18}$N$_2$O$_7$; C, 64.57, H, 4.06, N, 6.28; found C, 64.55, H, 4.01, N, 6.31.

Example 5

Ethyl-5-methyl-1-(2-nitrobenzoyl)pyrrolo[1,2-a]quinoline-3-carboxylate (3d

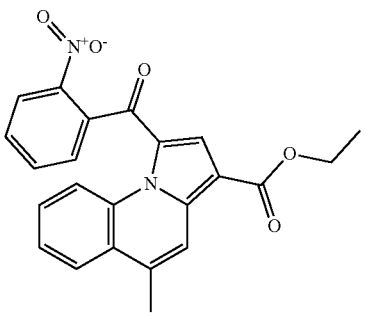

3d

Appearance; yellow color; FT-IR (neat cm$^{-1}$); 2979, 1705, 1698, 1633; $^1$H-NMR (800 MHz, CDCl$_3$); δ=8.31 (1H, s, H), 8.25 (1H, m, H), 8.21-8.12 (2H, Ar—H), 7.69-7.68 (1H, m, H), 7.67-7.62 (1H, m, H), 7.61-7.53 (3H, m, Ar—H), 7.28 (1H, s, H), 4.40-4.37 (2H, q, J=7.2 Hz, CH$_2$), 2.73 (3H, s, CH$_3$), 1.42-1.40 (3H, t, J=7.2 Hz, CH$_2$CH$_3$); $^{13}$C-NMR (200 MHz, CDCl$_3$); 184.6, 164.2, 140.5, 138.5, 136.5, 132.7, 130.1, 130.1, 129.9, 128.4, 128.4, 127.8, 125.4, 125.3, 125.2, 120.6, 117.3, 106.6, 60.1, 19.58; LC-MS (ESI, positive): m/z=403.2 (M+H)+; Anal. calcd for C$_{23}$H$_{18}$N$_2$O$_5$; C, 68.65, H, 4.51, N, 6.96; found C, 68.66, H, 4.58, N, 5.98.

Example 6

Ethyl-1-(4-bromobenzoyl)-5-methylpyrrolo[1,2-a]quinoline-3-carboxylate (3e

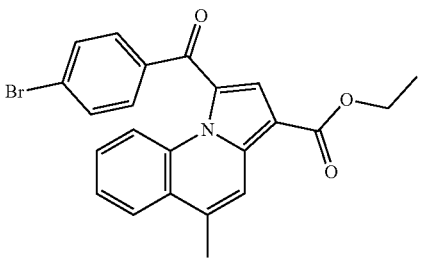

3e

Appearance; yellow color; FT-IR (neat cm$^{-1}$); 2973, 1704, 1632, 1539; $^1$H-NMR (800 MHz, CDCl$_3$); δ=8.25 (1H, s, H), 8.14 (1H, m, H), 7.98-7.97 (3H, m, Ar—H), 7.72-7.71 (2H, d, Ar—H), 7.62-7.54 (2H, m, H), 7.28 (1H, s, H), 4.41-4.37 (2H, q, J=7.2 Hz, CH$_2$), 2.73 (3H, s, CH$_3$), 1.42-1.40 (3H, t, J=7.2 Hz, CH$_3$); $^{13}$C-NMR (200 MHz, CDCl$_3$); 183.3, 164.1, 140.7, 137.4, 136.8, 132.9, 131.7, 131.5, 130.0, 128.5, 127.7, 127.3, 125.4, 125.4, 120.5, 117.2, 106.8, 60.1, 19.5, 14.5; LC-MS (ESI, positive):

m/z=436.2 (M+H)+, 438.2 (M+2H)+; Anal. calcd for C$_{23}$H$_{18}$BrNO$_3$; C, 63.32, H, 4.16, N, 3.21; found C, 63.30, H, 4.16, N, 3.28.

Example 7

Dimethyl-1-(4-cyanobenzoyl)-5-methylpyrrolo[1,2-a]quinoline-2,3-dicarboxylate (3f)

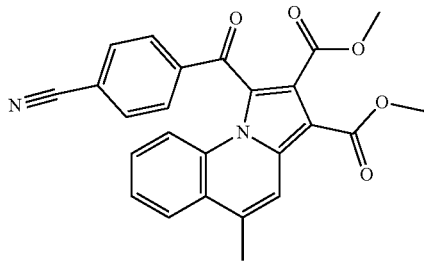

3f

Appearance; yellow color; FT-IR (neat cm$^{-1}$); 2957, 2232, 1737, 1703, 1646, 1535; $^1$H-NMR (800 MHz, CDCl$_3$); δ=8.22 (1H, d, H), 8.21-8.19 (2H, m, Ar—H), 7.78 (1H, s, H), 7.61-7.60 (2H, m, Ar—H), 7.51-7.47 (3H, m, H), 3.93 (3H, s, OCH$_3$), 3.49 (3H, s, OCH$_3$), 2.72 (3H, s, CH$_3$); $^{13}$C-NMR (200 MHz, CDCl$_3$); 185.0, 165.2, 163.4, 141.1, 138.1, 136.6, 132.3, 132.1, 130.2, 130.0, 128.9, 125.9, 125.7, 125.7, 124.8, 119.5, 117.8, 117.2, 116.6, 104.9, 52.4, 51.8, 19.5; LC-MS (ESI, positive): m/z=427.2 (M+H)+; Anal. calcd for C$_{25}$H$_{18}$N$_2$O$_5$; C, 70.42, H, 4.25, N, 6.57; found C, 70.54, H, 4.20, N, 6.60.

Example 8

Dimethyl-1-benzoyl-5-methylpyrrolo[1,2-a]quinoline-2,3-dicarboxylate (3g)

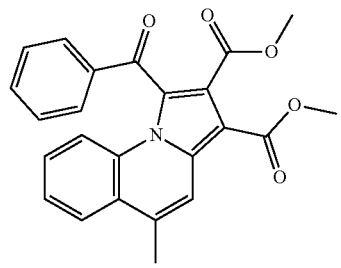

3g

Appearance; brick red color; FT-IR (neat cm$^{-1}$); 2952, 1726, 1702, 1634, 1445; $^1$H-NMR (800 MHz, CDCl$_3$); δ=8.21 (1H, s, H), 8.02-7.76 (5H, m, Ar—H), 7.51-7.43 (4H, m, Ar—H), 3.92 (3H, s, OCH$_3$), 3.45 (3H, s, OCH$_3$), 2.70 (3H, s, CH$_3$); $^{13}$C-NMR (200 MHz, CDCl$_3$); 187.4, 165.3, 163.8, 137.7, 137.4, 135.5, 133.7, 132.3, 129.8, 128.7, 128.6, 128.5, 126.0, 125.6, 125.5, 119.5, 117.3, 104.4, 52.2, 51.6, 19.5; LC-MS (ESI, positive): m/z=402.2 (M+H)+; Anal. calcd for C$_{24}$H$_{19}$NO$_5$; C, 71.81, H, 4.77, N, 3.49; found C, 71.82, H, 4.71, N, 3.58.

Example 9

Ethyl-1-benzoyl-5-methylpyrrolo[1,2-a]quinoline-3-carboxylate (3h)

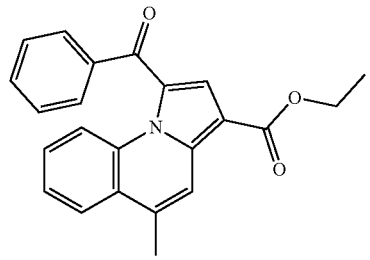

3h

Appearance; yellow color; FT-IR (neat cm$^{-1}$); 2980, 1700, 1634, 1465; $^1$H-NMR (800 MHz, CDCl$_3$); δ=8.25 (1H, s, H), 8.18-8.10 (3H, m, Ar—H), 8.01-8.00 (1H, m, H), 7.90-7.89 (1H, m, Ar—H) 7.68-7.53 (5H, m, Ar—H), 4.40-4.37 (2H, q, J=7.2 Hz, CH$_2$), 2.73 (3H, s, CH$_3$), 1.58-1.27 (3H, t, J=7.2 Hz, CH$_2$CH$_3$); $^{13}$C-NMR (200 MHz, CDCl$_3$); 184.6, 164.2, 140.5, 138.5, 136.5, 133.0, 132.7, 130.1, 129.9, 128.4, 128.4, 127.8, 125.4, 125.3, 125.2, 120.6, 117.3, 106.6, 60.1, 19.5, 14.5; LC-MS (ESI, positive): m/z=358.2 (M+H)+; Anal. calcd for C$_{23}$H$_{19}$NO$_3$; C, 77.29, H, 5.36, N, 3.92; found C, 77.24, H, 5.21, N, 3.99.

Example 10

Dimethyl-1-(4-fluorobenzoyl)-5-methylpyrrolo[1,2-a]quinoline-2,3-dicarboxylate (3i)

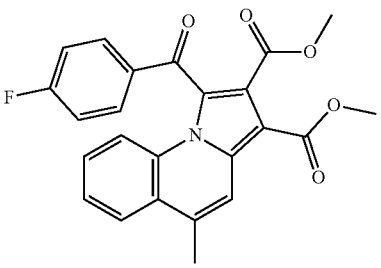

3i

Appearance; golden yellow color; FT-IR (neat cm$^{-1}$); 2956, 1737, 1704, 1643, 1598; $^1$H-NMR (800 MHz, CDCl$_3$); δ=8.15 (1H, d, H), 8.10-7.92 (2H, m, Ar—H), 7.65-7.45 (4H, m, H), 7.19-7.16 (2H, s, Ar—H), 3.92 (3H, m, OCH$_3$), 3.52 (3H, s, OCH$_3$), 2.70 (3H, s, CH$_3$); $^{13}$C-NMR (200 MHz, CDCl$_3$); 185.8, 166.7, 165.4, 163.7, 137.4, 135.6, 134.1, 132.5, 132.5, 132.2, 128.7, 128.5, 125.6, 125.5, 119.4, 117.3, 115.9, 115.8, 104.4, 52.3, 51.7, 19.5; LC-MS (ESI, positive): m/z=420.2 (M+H)+; Anal. calcd for C$_{24}$H$_{18}$FNO$_5$; C, 68.73, H, 4.33, N, 3.34; found C, 68.76, H, 4.27, N, 3.38.

The physicochemical characteristics of the ethyl-1-(substituted benzoyl)-5-methylpyrrolo[1,2-a]quinoline-3-carboxylates (3a-i) are listed in Table 1.

TABLE 1

| Compound code | Molecular formulae (molecular mass) | R | $R^1$ | $R^2$ | Yield (%)[a,b] | m.p. (° C.) |
|---|---|---|---|---|---|---|
| 3a | $C_{26}H_{17}F_6NO_5$ (537) | 3,5-$CF_3$ | $CH_3$ | $COOCH_3$ | 66.5 | 188-189 |
| 3b | $C_{25}H_{17}F_6NO_3$ (493) | 3,5-$CF_3$ | $C_2H_5$ | H | 53.7 | 174-175 |
| 3c | $C_{24}H_{18}N_2O_7$ (446) | 2-$NO_2$ | $CH_3$ | $COOCH_3$ | 61.8 | 186-188 |
| 3d | $C_{23}H_{18}N_2O_5$ (402) | 2-$NO_2$ | $C_2H_5$ | H | 54.8 | 182-186 |
| 3e | $C_{23}H_{18}BrNO_3$ (435) | 4-Br | $C_2H_5$ | H | 55.0 | 186-187 |
| 3f | $C_{25}H_{18}N_2O_5$ (426) | 4-CN | $CH_3$ | $COOCH_3$ | 66.7 | 184-185 |
| 3g | $C_{24}H_{19}NO_5$ (401) | 4-H | $CH_3$ | $COOCH_3$ | 65.5 | 158-160 |
| 3h | $C_{23}H_{19}NO_3$ (357) | 4-H | $C_2H_5$ | H | 58.9 | 154-156 |
| 3i | $C_{24}H_{18}FNO_5$ (419) | 4-F | $CH_3$ | $COOCH_3$ | 63.9 | 196-197 |

[a] All the synthetic compounds were characterized by physical and spectral data
[b] Yield was calculated after column chromatography purification and confirmation Anticancer Activity

Example 11

The human breast cancer cell line (MCF-7), and adeno carcinomic human alveolar basal epithelial cell line (A-549), were used in the present study for the investigation of cell viability assay of the synthesized compounds.

The cells were seeded in a 96-well flat-bottom microplate and maintained at 37° C. in 95% humidity and 5% $CO_2$ overnight. The microplates were then treated with different concentrations (5-100 μM) of the samples. The cells were incubated for another 48 h. The wells were washed twice with PBS and 20 μL of the MTT staining solution was added to each well and the plate was incubated at 37° C. After 4 h, 100 μL of DMSO was added to each well to dissolve the formazan crystals and absorbance was recorded with a 570 nm using a microplate reader.

In vitro cytotoxicity was performed by 3-(4,5-dimethylthiazol-2-yl)-2,5-di-phenyltetrazolium bromide (MTT) assay. Tested compounds were dissolved in DMSO by heating at 95° C. for 10 min, cooled at room temperature and final stock concentration of 1 mg/mL was prepared in DMEM (final DMSO concentration was <1%). The stock solutions were serially diluted to obtain the concentration range of 25 to 400 μM using DMEM, and cells were treated in triplicates. Untreated cells represented a control group and pac. treated as a positive control. After 48 h of incubation, the media was aspirated, 100 μL MTT (1 mg/mL) was added to each well and the plate was incubated at 37° C. for 4 h. After incubation, the media/MTT solution was aspirated and 100 μL DMSO was added to all the wells. Using a multi-mode microplate reader, a uniform shaking (for 5 min) was applied to dissolve Formazan crystals and the absorbance was recorded at 570 nm. Cell viability was calculated using the following equation:

$$\text{Surviving cells (\%)} = \frac{\text{Mean } OD \text{ of test compound}}{\text{Mean } OD \text{ of negative control}} \times 100$$

The 50% minimum inhibitory concentration ($IC_{50}$) was determined using Prism software version 7. Using graph Pad Prism Version 5.1, $IC_{50}$ values of the compounds were calculated.

Statistical analysis of the cytotoxicity data was performed on GraphPad Prism. All cytotoxicity experiments were conducted in triplicates. Results were analyzed as the standard error of the mean (SEM) and one-way analysis of variance (ANOVA) and the Dunnet multiple comparison test was used to evaluate the treated groups and the control. Further Bonferroni post-tests were performed for comparison of the complex with cis-platin. Differences were considered significant when $p<0.05$.

The anticancer $IC_{50}$ values of the title compounds (3a, 3b, 3c, 3d and 3i) in μM against the human breast cancer cell line (MCF-7), adeno carcinomic human alveolar basal epithelial cell line (A-549) are listed in Table 2.

TABLE 2

| Compound Code | Compound structure | MCF-7 (μM) | A-549 (μM) |
|---|---|---|---|
| 3a | 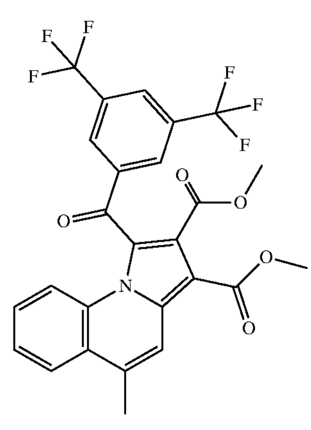 [SMILES: COC(=O)c1c(C(=O)OC)c2cc(C)c3ccccc3n2c1C(=O)c1cc(C(F)(F)F)cc(C(F)(F)F)c1] | 0.272 | 0.433 |

TABLE 2-continued

| Compound Code | Compound structure | MCF-7 (μM) | A-549 (μM) |
| --- | --- | --- | --- |
| 3b | 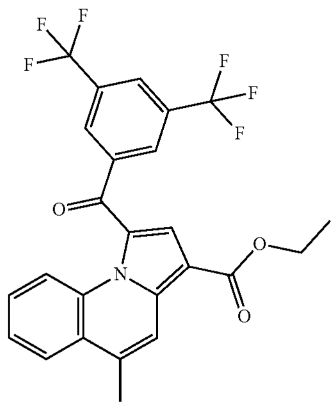 [SMILES: CCOC(=O)c1cc(C(=O)c2cc(C(F)(F)F)cc(C(F)(F)F)c2)n2c1cc(C)c1ccccc12] | 0.027 | 0.099 |
| 3c | 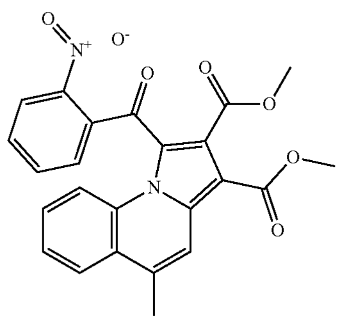 | 0.015 | 0.316 |
| 3d | 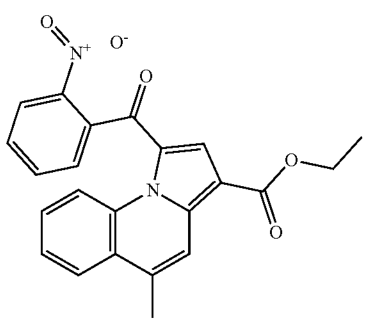 | 0.085 | 0.291 |
| 3i | 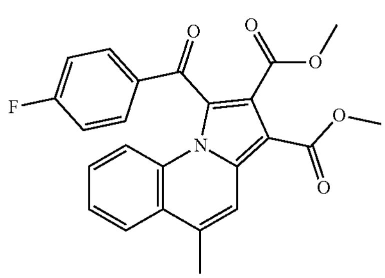 [SMILES: COC(=O)c1c(C(=O)OC)c2cc(C)c3ccccc3n2c1C(=O)c1ccc(F)cc1] | 0.209 | 0.183 |

We claim:

1. A method of treating cancer in a patient, the method comprising administering a therapeutically effective of a compound to a patient in need thereof, the compound having the formula I:

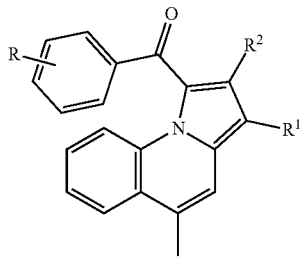

or a pharmaceutically acceptable salt, ester, stereoisomer, or solvate thereof, wherein:
one or more R groups can be attached to the phenyl ring, wherein each R is independently selected from the group consisting of hydrogen, one or more halogens, cyano, nitro, and trihalomethyl;
$R_1$ is —COOCH$_3$ or —COOCH$_2$CH$_3$; and
$R_2$ is —COOCH$_3$;
wherein the cancer is selected from the group consisting of breast cancer, lung cancer, and a combination thereof.

2. The method of treating cancer of claim 1, wherein R is selected from the group consisting of hydrogen, trifluoromethyl, NO$_2$, CN, bromine, and fluorine.

3. The method of treating cancer of claim 1, wherein one or two R groups is attached to the phenyl ring.

4. The method of treating cancer of claim 3, wherein two R groups are attached to the phenyl ring and are both trifluoromethyl.

5. The method of treating cancer of claim 3, wherein one R group is attached to the phenyl ring and is selected from the group consisting of hydrogen, NO$_2$, CN, bromine, and fluorine.

6. The method of treating cancer of claim 1, wherein R is selected from the group consisting of hydrogen, 3,5-bis(trifluoromethyl), 4-CN, 4-Br, 2-NO$_2$, and 4-F.

7. The method of treating cancer of claim 1, wherein $R_1$ and $R_2$ are both —COOCH$_3$.

8. The method of treating cancer of claim 1, wherein $R_1$ and $R_2$ are both —COOCH$_3$ and R is selected from the group consisting of 3,5-bis(trifluoromethyl), 2-NO$_2$, 4-CN, hydrogen, and 4-F.

9. The method of treating cancer of claim 1, wherein the compound is selected from the group consisting of:
Dimethyl-1-(3,5-bis(trifluoromethyl)benzoyl)-5-methylpyrrolo[1,2-a]quinoline-2,3-dicarboxylate (3a),
Dimethyl-5-methyl-1-(2-nitrobenzoyl)pyrrolo[1,2-a]quinoline-2,3-dicarboxylate (3c),
Dimethyl-1-(4-cyanobenzoyl)-5-methylpyrrolo[1,2-a]quinoline-2,3-dicarboxylate (3f),
Dimethyl-1-benzoyl-5-methylpyrrolo[1,2-a]quinoline-2,3-dicarboxylate (3g),
Dimethyl-1-(4-fluorobenzoyl)-5-methylpyrrolo[1,2-a]quinoline-2,3-dicarboxylate (3i),
and a pharmaceutically acceptable salt, ester, stereoisomer, or solvate thereof.

10. A method of treating cancer in a patient, the method comprising administering a therapeutically effective of a compound to a patient in need thereof, the compound having the formula I:

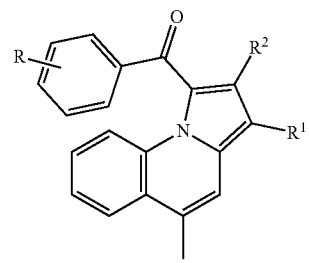

or a pharmaceutically acceptable salt, ester, stereoisomer, or solvate thereof, wherein:
one or more R groups can be attached to the phenyl ring, wherein each R is independently selected from the group consisting of hydrogen, fluorine, bromine, cyano, nitro, and trifluoromethyl;
$R_1$ is —COOCH$_3$ or —COOCH$_2$CH$_3$; and
$R_2$—COOCH$_3$;
wherein the cancer is selected from the group consisting of breast cancer, lung cancer, and a combination thereof.

11. A method of treating cancer in a patient, the method comprising administering a therapeutically effective of a compound to a patient in need thereof, the compound being selected from the group consisting of:
Dimethyl-1-(3,5-bis(trifluoromethyl)benzoyl)-5-methylpyrrolo[1,2-a]quinoline-2,3-dicarboxylate (3a),
Dimethyl-5-methyl-1-(2-nitrobenzoyl)pyrrolo[1,2-a]quinoline-2,3-dicarboxylate (3c),
Dimethyl-1-(4-cyanobenzoyl)-5-methylpyrrolo[1,2-a]quinoline-2,3-dicarboxylate (3f),
Dimethyl-1-benzoyl-5-methylpyrrolo[1,2-a]quinoline-2,3-dicarboxylate (3g),
Dimethyl-1-(4-fluorobenzoyl)-5-methylpyrrolo[1,2-a]quinoline-2,3-dicarboxylate (3i),
and a pharmaceutically acceptable salt, ester, stereoisomer, or solvate thereof;
wherein the cancer is selected from the group consisting of breast cancer, lung cancer, and a combination thereof.

* * * * *